United States Patent [19]
Savord et al.

[11] Patent Number: 5,993,390
[45] Date of Patent: Nov. 30, 1999

[54] SEGMENTED 3-D CARDIAC ULTRASOUND IMAGING METHOD AND APPARATUS

[75] Inventors: Bernard J. Savord; Karl E. Thiele, both of Andover, Mass.

[73] Assignee: Hewlett- Packard Company, Palo Alto, Calif.

[21] Appl. No.: 09/156,110

[22] Filed: Sep. 18, 1998

[51] Int. Cl.$^6$ ..................................................... A61B 8/00
[52] U.S. Cl. .......................................... 600/437; 128/916
[58] Field of Search .................................... 600/437, 455, 600/441, 453, 458, 436, 454, 443, 447, 515, 513, 442; 128/916

[56] References Cited

U.S. PATENT DOCUMENTS

| | | | |
|---|---|---|---|
| 5,159,931 | 11/1992 | Pini | 600/443 |
| 5,315,512 | 5/1994 | Roth | 600/442 |
| 5,337,752 | 8/1994 | Reeves | 600/515 |
| 5,435,310 | 7/1995 | Sheehan et al. | 600/437 |

OTHER PUBLICATIONS

Takahiro Ota et al, Novel Determinatin of Left Ventricular Vol. by Tracing Arbitrary Planes Using Real–Time, 3D Echocardiography: In Vitro and In Vivo Validation, 70th Scientific Session American Heart Assn. Meeting, Nov. 11, 1997, p. 1832.

Takahiro Ota et al, "Accuracy of Left Ventricular Stroke Volume Measurement Using Real–Time, Three Dimensional Echocardiography & Electromagnetic Flow Probe in Vivo", 70th Scientific Session American Heart Assn. Meeting, Nov. 11, 1997, p. 1831.

Craig E. Fleishman et al, "Evaluation of Atrioventricular Valve Abnormalities Using Real–Time Three–Dimensinal Echocardiography", 70th Scientific Session American Heart Assn. Meeting, Nov. 11, 1997, p. 1045.

Ming Shu et al, "Tricuspid Velocity Profiles Reflect Right Ventricular Diastolic Wall MOtion Abnormalities: Real--Time 3D Echocardiography and Computational Fluid Dynamics", 70th Scientific Session American Heart Assn. Meeting, Nov. 11, 1997, p. 2990.

Takahiro Shiota et al, "Application of a New Real–Time Three–Dimensional Method for Evaluating Right Ventricular Stroke Volume", 70th Scientific Session American Heart Assn. Meeting, Nov. 11, 1997, p. 1830.

*Primary Examiner*—Scott M. Getzow
*Assistant Examiner*—Maulin Patel

[57] ABSTRACT

Ultrasound image data representative of three-dimensional volume segments of an image volume of interest is acquired in synchronism with corresponding cardiac cycles of a patient. The image data representative of the volume segments is combined to provide image data representative of a three-dimensional image of the image volume. The image data acquisition may be synchronized to a selected phase of the patient's cardiac cycle, so that the image represents the image volume at the selected phase. Image data for a three-dimensional volume segment may be acquired during each of the cardiac phases of a cardiac cycle.

34 Claims, 8 Drawing Sheets

SEGMENTED 3-D CARDIAC ULTRASOUND IMAGING METHOD AND APPARATUS

FIELD OF THE INVENTION

This invention relates to medical ultrasound imaging and, more particularly, to methods and apparatus for three-dimensional cardiac ultrasound imaging.

BACKGROUND OF THE INVENTION

Medical ultrasound imaging systems typically use a one-dimensional phased array to form an image of a two-dimensional slice through a patient's body. This approach has limitations. First, the two-dimensional slice is always perpendicular to the face of the transducer, thereby limiting the choice of views. Second, anatomy such as the left ventricle is inherently three-dimensional. To obtain an accurate volume measurement of the left ventricle, three-dimensional data must be acquired. A goal in three-dimensional cardiac imaging is to obtain a measure of the volume of the left ventricle in both end systole and end diastole, so that ejection fraction and cardiac output can be estimated.

In current solutions, such as Hewlett Packard's Sonos 5500, a two-dimensional slice of data is acquired per cardiac phase each heartbeat. For a volume of 120 two-dimensional slices, 120 heartbeats are required to gather the volume data. Cardiac, respiratory, patient whole body and sonographer motion occur during this long acquisition. Cardiac motion may be frozen by using an ECG trigger. Respiratory motion may be reduced through the use of either multiple breath-holds or respiratory gating. However, since the heart does not return to the same position from breath to breath or from breathhold to breathhold, discontinuities are introduced into the acquired data. Patient and sonographer motion also cause discontinuities and overall geometric distortion.

A system capable of acquiring real time three-dimensional data by electronically steering in two dimensions is described by T. Ota et al. in "Accuracy of Left Ventricular Stroke Volume Measurement Using Real-Time, Three Dimensional Echocardiography Flow Probe in Vivo", 70th Scientific Session American Heart Association Meeting, Nov. 11, 1997. This system uses 512 active transducer elements. Signals from the transducer elements are passed through a cable having 512 coaxial conductors into a system with appropriate electronics. The image quality of the system is limited due to the small number of transducer elements used.

Apparatus for obtaining a three-dimensional reconstruction of anatomic structures through the acquisition of two-dimensional ultrasound images is disclosed in U.S. Pat. No. 5,159,931 issued Nov. 3, 1992 to Pini. One or more two-dimensional images are acquired during alternate heartbeats of a patient. When more than one two-dimensional image is acquired during a single heartbeat, the images represent a constant two-dimensional slice of the patient's heart at different phases of the cardiac cycle. During alternate heartbeats when images are not being acquired, the transducer is rotated to a new position. Rotation of the transducer may be performed mechanically using a stepping motor or electronically using a matrix or multiple arrays of transducer elements. Acquisition of a three-dimensional image requires 120 heartbeats.

All of the known prior art three-dimensional cardiac imaging techniques have had low resolution and/or long acquisition times. In the case of long acquisition times, the images typically exhibit discontinuities due to cardiac, respiratory, patient and/or sonographer movement. Accordingly, there is a need for improved methods and apparatus for three-dimensional cardiac ultrasound imaging.

SUMMARY OF THE INVENTION

According to a first aspect of the invention, a method for cardiac ultrasound imaging is provided. The method comprises the steps of acquiring ultrasound image data representative of three-dimensional volume segments of an image volume of interest in a patient in synchronism with corresponding cardiac cycles of the patient, and combining the image data representative of the volume segments to provide image data representative of a three-dimensional ultrasound image of the image volume. The image data acquisition is preferably synchronized to a selected phase of the patient's cardiac cycle, so that the image represents the image volume at the selected phase.

In one embodiment, image data is acquired for abutting volume segments in synchronism with successive cardiac cycles of the patient. The three-dimensional image may be displayed following completion of image data acquisition for the image volume.

In another embodiment, image data is acquired for interleaved volume segments in synchronism with successive cardiac cycles of the patient. A low resolution image of the image volume may be displayed during image data acquisition for the interleaved volume segments. A high resolution image may be displayed following completion of image data acquisition for the interleaved volume segments.

Image data for a three-dimensional volume segment may be acquired during each of the phases of a cardiac cycle. Image data may be acquired for different ones of the three-dimensional volume segments during different cardiac cycles. The volume segment image data for respective cardiac phases may be combined to provide three-dimensional images representative of the cardiac phases.

In a further feature of the invention, the volume segments of the image volume may overlap. The volume segments may be aligned by analyzing the sets of image data in overlapping portions of the volume segments.

According to a further feature of the invention, image data corresponding to different volume segments of the image volume may be acquired with different apertures of an ultrasound transducer.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
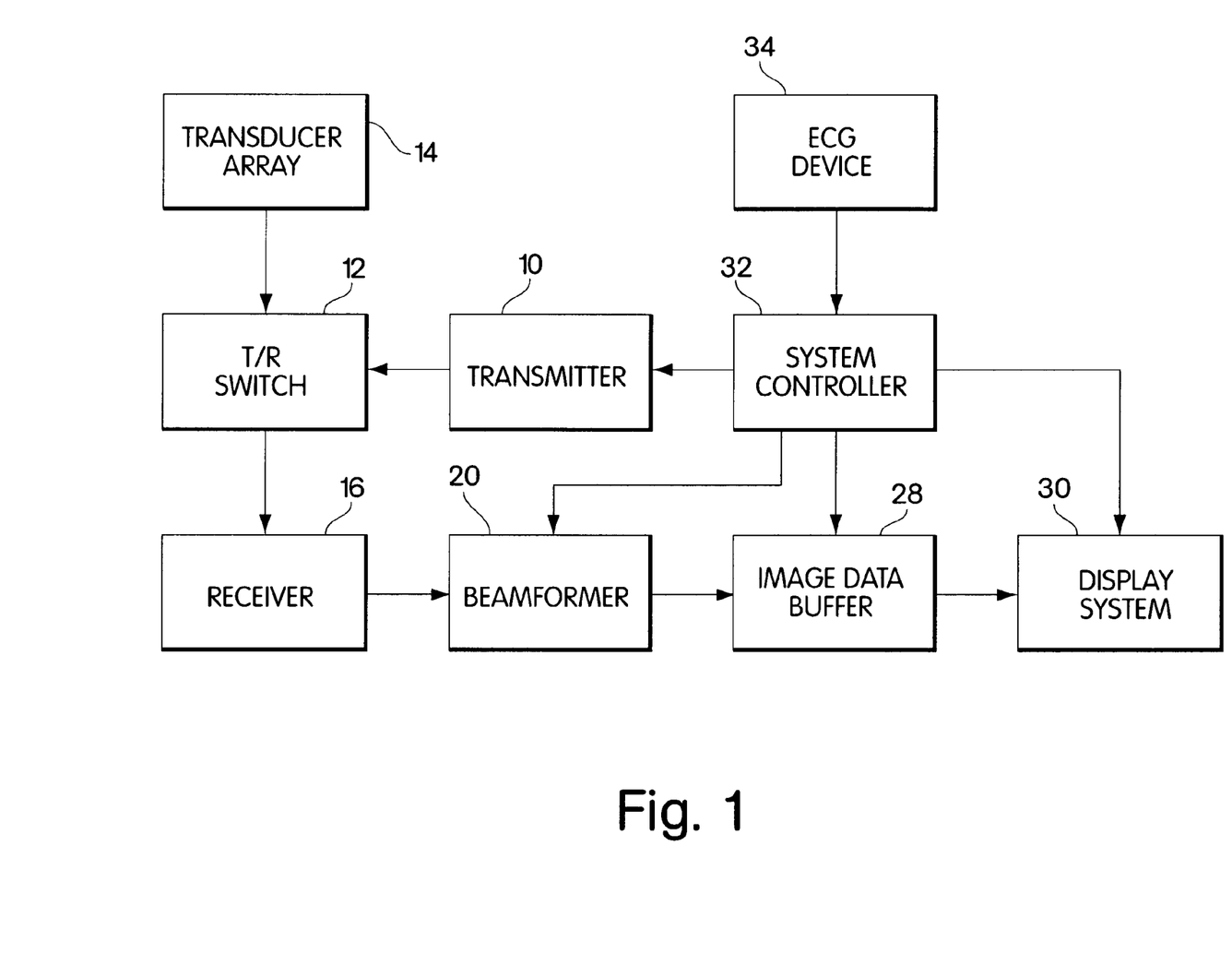
FIG. 1 is a block diagram of an example of an ultrasound imaging system suitable for implementing the present invention.

A simplified block diagram of an example of an ultrasound imaging system suitable for implementing the present invention is shown in FIG. 1. An ultrasound transmitter 10 is coupled through a transmit/receive (T/R) switch 12 to a transducer array 14. Transducer array 14 may be a two-dimensional array of transducer elements for performing three-dimensional scanning. The transducer array 14 transmits ultrasound energy into a region being imaged and receives reflected ultrasound energy, or echos, from various structures and organs within the patient's body. The transmitter 10 includes a transmit beamformer. By appropriately delaying the pulses applied to each transducer element by transmitter 10, the transmitter 10 transmits a focused ultrasound beam along a desired transmit scan line.

The transducer array 14 is coupled through T/R switch 12 to an ultrasound receiver 16. Reflected ultrasound energy from a given point within the patient's body is received by the transducer elements at different times. The transducer elements convert the received ultrasound energy to received electrical signals which are amplified by receiver 16 and are supplied to a receive beamformer 20. The signals from each transducer element are individually delayed and then are summed by the beamformer 20 to provide a beamformer signal that is a representation of the reflected ultrasound energy level along a given receive scan line. As known in the art, the delays applied to the received signals may be varied during reception of ultrasound energy to effect dynamic focusing. The process is repeated for multiple scan lines to provide signals for generating an image of a region of interest in the patient's body. Because the transducer array is two-dimensional, the receive scan lines can be steered in azimuth and in elevation to form a three-dimensional scan pattern. The beamformer 20 may, for example, be a digital beamformer of the type used in the HP Sonos 5500 Ultrasound Imaging System, manufactured and sold by Hewlett-Packard Company.

The beamformer signals are stored in an image data buffer 28 which, as described below, stores image data for different volume segments of an image volume and for different cardiac phases of a cardiac cycle. The image data is output from image data buffer 28 to a display system 30 which generates a three-dimensional image of the region of interest from the image data. The display system 30 may include a scan converter which converts sector scan signals from beamformer 20 to conventional raster scan display signals.

A system controller 32 provides overall control of the system. The system controller 32 performs timing and control functions and typically includes a microprocessor and associated memory.

An ECG device 34 includes ECG electrodes attached to the patient. The ECG device 34 supplies ECG waveforms to system controller 32 for synchronizing imaging to the patient's cardiac cycle, as described in detail below.

Figure 2:
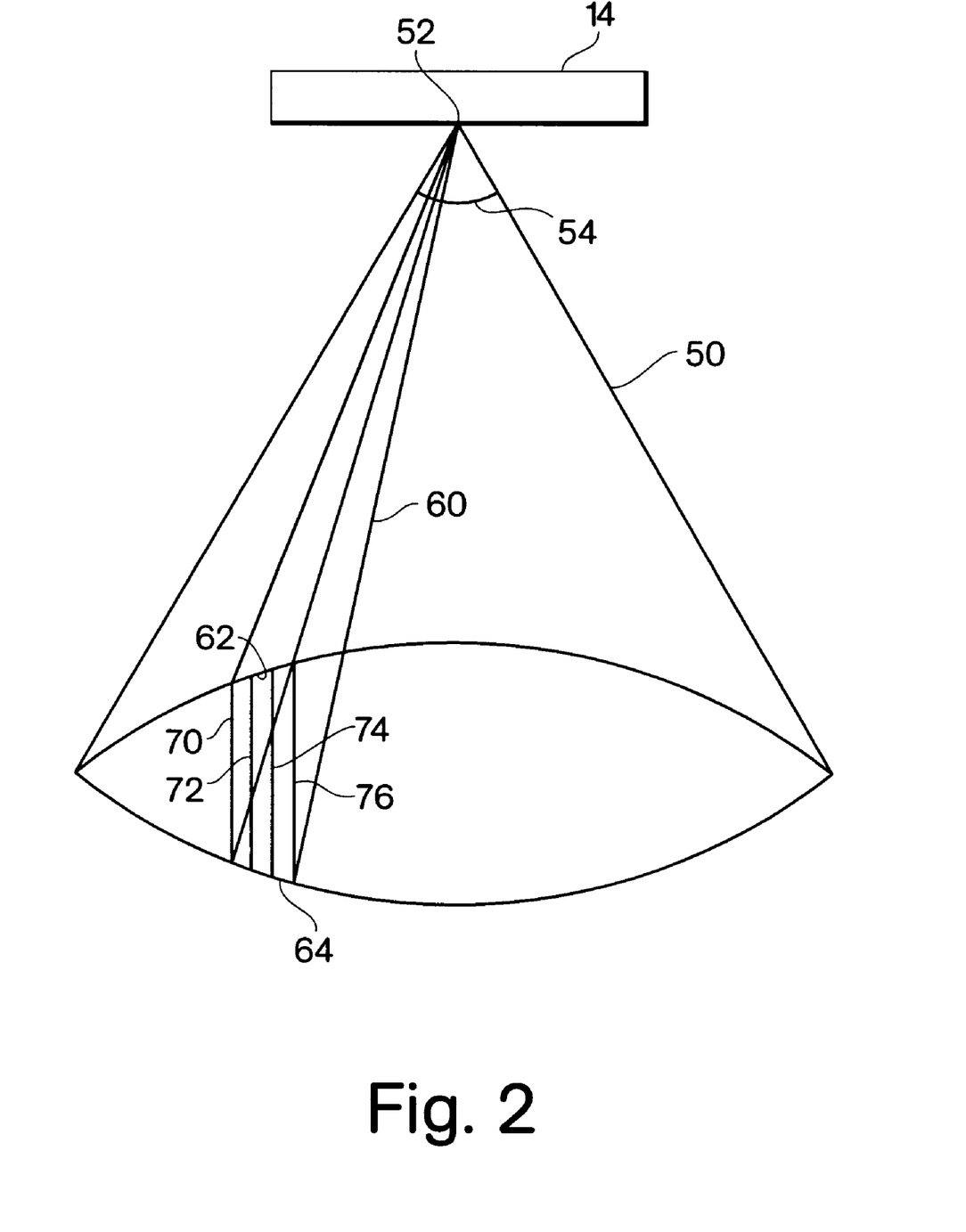
FIG. 2 is a schematic representation of a three-dimensional image volume and a volume segment of the image volume.

An example of a three-dimensional image volume for which an image may be acquired in accordance with the present invention is shown in FIG. 2. An image volume 50 may have a conical shape with an apex 52 centered on transducer array 14. Image data for image volume 50 may be acquired by three-dimensional ultrasound imaging. Volume 50 may, for example, be imaged as a plurality of two-dimensional sector-shaped slices. The diameter of conical image volume 50 may be defined in terms of the required number of receive lines to achieve a desired resolution. The required number of receive lines to acquire a complete image of volume 50 is given by $\pi L^2/4$, where L is the diameter of conical image volume 50 in units of receive lines. Thus, for example, where image volume 50 has a diameter of 120 receive lines, 11,304 receive lines are needed to acquire image data for volume 50.

The present invention relates to cardiac imaging. To facilitate cardiac imaging, image volume 50 may be divided into three-dimensional volume segments for imaging of the patient's heart. An example of a volume segment is illustrated in FIG. 2. Volume segment 60 is a three-dimensional slice of conical image volume 50, and may be imaged as a series of two-dimensional sector-shaped slices 70, 72, 74 and 76. The entire image volume 50 is divided into volume segments.

The volume segments which constitute image volume 50 may have any desired size and shape. Thus, for example, the cross-sections of the volume segments may be square, rectangular, circular, or irregularly shaped. Furthermore, different volume segments may have different sizes and shapes within a single image volume. In addition, the volume segments are not necessarily imaged as a series of two-dimensional slices. All that is required is that a sufficient number of transmit and receive lines be utilized to obtain a desired image resolution. The imaging protocol may use any desired pattern or may be random. For a given image volume, the selection of the size, shape and number of volume segments may be based in part on the time available for image data acquisition during a specified cardiac phase as described below. Image data corresponding to different volume segments may be acquired with different apertures of transducer array 14.

It will be understood that the image volume itself is not limited to a conical shape and may have a variety of different shapes and sizes. For example, the image volume may be a pyramid or a truncated pyramid. The selection of the size and shape of the image volume may be based on the application and the type of transducer being utilized.

Figure 3:
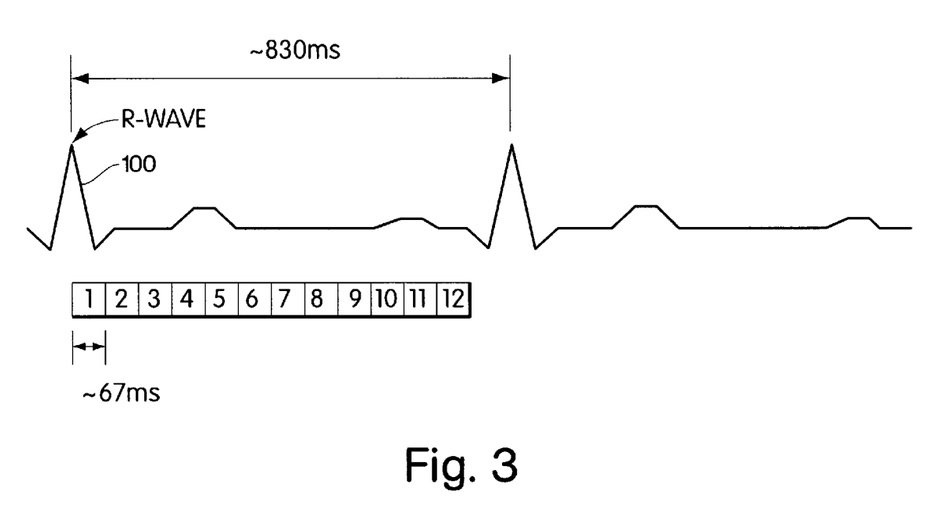
FIG. 3 shows an ECG waveform that is divided into twelve cardiac phases.

A feature of the invention is based on acquisition of image data for one or more volume segments in synchronism with the patient's cardiac cycle. An example of an ECG waveform is shown in FIG. 3. In the example of FIG. 3, ECG waveform 100 indicates a heartbeat every 830 milliseconds. The cardiac cycle may be divided into cardiac phases for imaging. In one example, 12 cardiac phases of approximately 67 milliseconds each may be utilized. The selection of the cardiac phase duration is typically based on the maximum time in which the heart does not move significantly. More or fewer cardiac phases may be utilized.

By obtaining a three-dimensional image representing the heart in each of the cardiac phases, a variety of information can be obtained. The three-dimensional images of the heart at successive cardiac phases can be displayed as a function of time to represent heart movement. The moving image can be used to identify end systole and end diastole and to perform other diagnostics. Images for a selected cardiac phase can be rotated to a desired orientation for improved analysis. Image analysis techniques can be utilized to quantify maximum and minimum volumes of the left ventricle. From this information, ejection volume and ejection fraction can be calculated.

In accordance with an aspect of the invention, image data for three-dimensional volume segments of the image volume is acquired during successive cardiac cycles until a complete image is acquired. The ECG waveform of the patient is used to trigger image data acquisition, so that data acquisition is synchronized to the patient's cardiac cycle. More specifically, image data acquisition is synchronized to a specific phase of the cardiac cycle. Furthermore, image data may be acquired during each phase of each cardiac cycle. The amount of image data acquired during each cardiac phase is a function of the duration of the cardiac phase and the speed of image data acquisition.

Referring again to the example of FIG. 2, assume that conical image volume 50 has an angle 54 of 90 and is 16 centimeters deep. For this image volume and a sound speed of 1540 meters per second, three-dimensional image data may be acquired in 587 milliseconds. This imaging time is based on the use of parallel receive techniques in which four receive lines are processed for each transmit event. Accordingly, approximately one ninth of the image data for image volume 50 may be acquired during a cardiac phase of 67 milliseconds, and image data for a complete three-dimensional image of the image volume is acquired in nine heartbeats. Image data for a volume segment may be acquired during one or more cardiac phases of a single cardiac cycle. That is, image data acquisition for a specified volume segment may be repeated during each cardiac phase. Thus, in nine heartbeats a complete three-dimensional image may be acquired for each of the 12 cardiac phases, for a total of 12 three-dimensional images. The image data may be stored in image data buffer 28 (FIG. 1) and combined into images following data acquisition. The total acquisition time in this example is 7.5 seconds, thereby minimizing motion problems and allowing image data to be acquired in one breathold.

Figure 4:
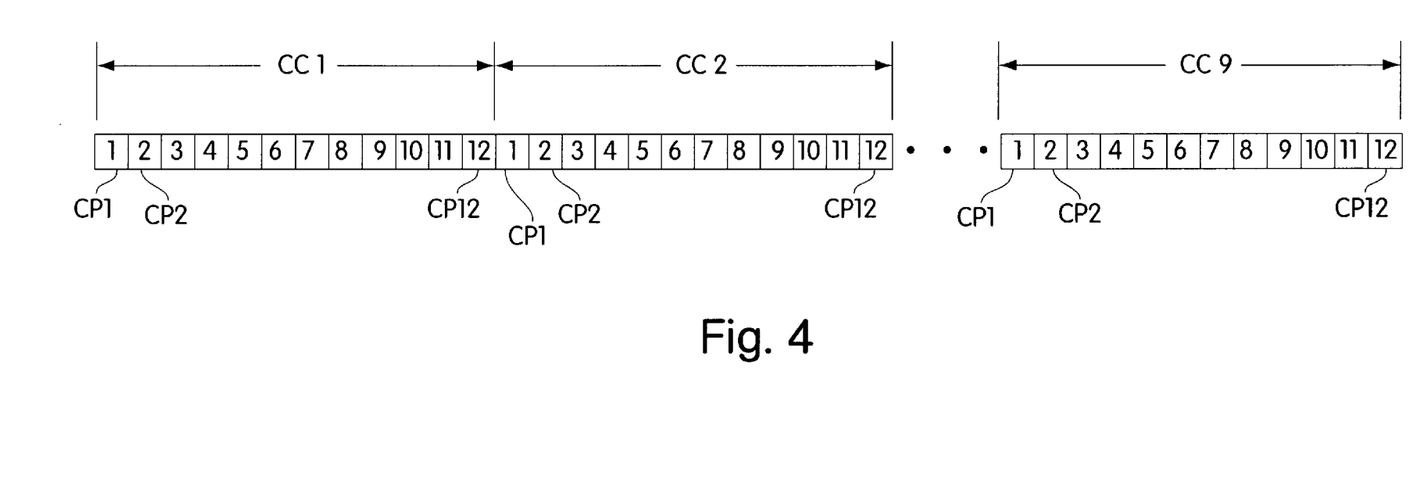
FIG. 4 shows an example of an ECG waveform wherein a three-dimensional image is acquired in nine heartbeats.

The acquisition of the image data for the nine volume segments which constitute the image volume is described with reference to FIGS. 3 and 4. The image volume is defined as having volume segments VS1–VS9. Each cardiac cycle is defined as having cardiac phases CP1–CP12. Image data is acquired during cardiac cycles CC1–CC9. Using this notation, image data for volume segment VS1 is acquired during cardiac phase CP1 of cardiac cycle CC1. Image data acquisition for volume segment VS1 is repeated during cardiac phases CP2–CP12 of cardiac cycle CC1. Image data for volume segment VS2 is similarly acquired during each of cardiac phases CP1–CP12 of cardiac cycle CC2. The same approach is used for cardiac cycle CC3–CC9, so that image data for volume segment VS9 is acquired during each of cardiac phases CP1–CP12 of cardiac cycle CC9. All of the image data is stored in image data buffer 28.

The image data stored in image data buffer 28 is organized and combined to form a three-dimensional image of the image volume in each cardiac phase. Thus, image data for volume segments VS1 through VS9, acquired during cardiac phase CP1 of cardiac cycles CC1–CC9, is combined to provide a three-dimensional image of cardiac phase CP1. Similarly, image data for volume segments VS1 through VS9, acquired during cardiac phase CP2 of cardiac cycles CC1–CC9, is combined to provide a three-dimensional image of cardiac phase 2. The same approach is used for cardiac phases CP3–CP12. Thus, 12 three-dimensional images of the 12 cardiac phases are obtained in nine heartbeats.

As indicated above, the image volume may be divided into a different number of volume segments. Furthermore, the cardiac cycle may be divided into a different number of cardiac phases. Image data for a single larger volume segment or for two or more smaller volume segments may be acquired during a cardiac cycle. The selection of these parameters depends on a number of factors, including the desired resolution, the imaging speed, i.e., the time to acquire a complete three-dimensional image, and the size of the image volume.

Figure 5:
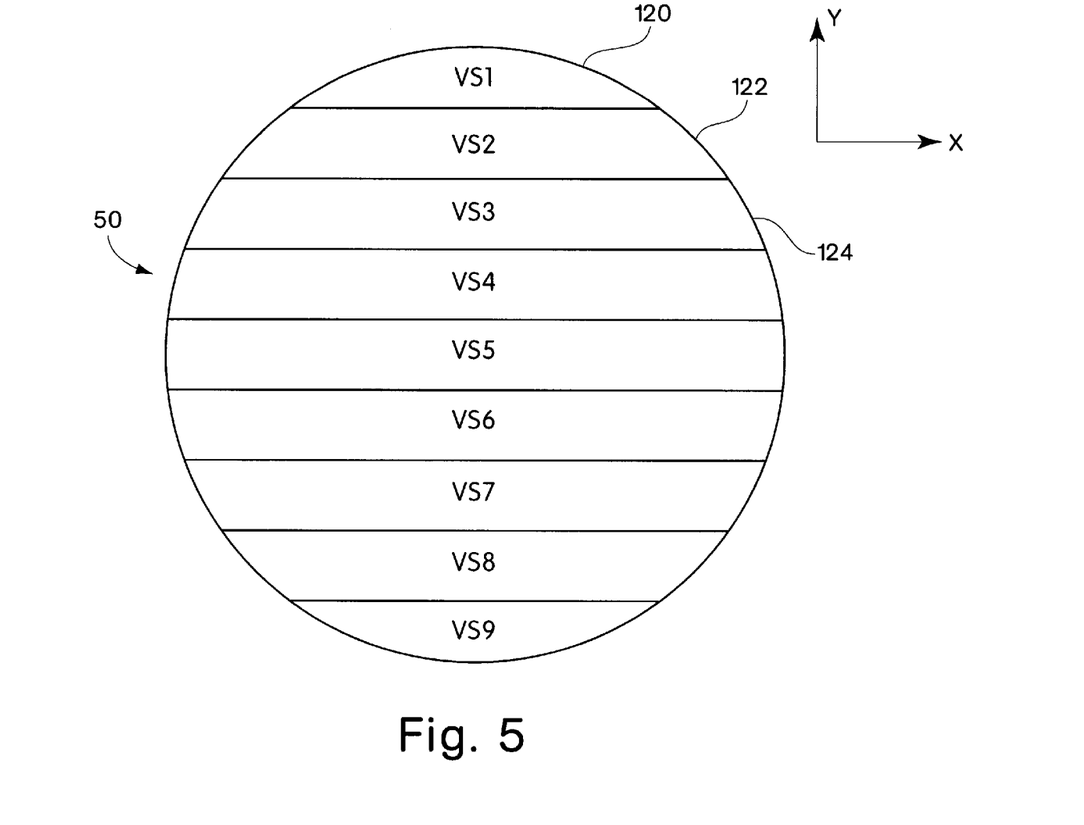
FIG. 5 is a cross-sectional view of a three-dimensional image volume that is divided into abutting volume segments.

Different imaging protocols may be used to acquire volume segment image data. An example of an imaging protocol using abutting volume segments is shown in FIG. 5. A cross section of conical image volume 50 is shown. Volume segments 120, 122, 124, etc. comprise abutting, three-dimensional slices of the conical image volume. Each of the volume segments 120, 122, 124, etc. may be imaged as a series of two-dimensional sector-shaped slices. Nine volume segments constitute the image volume 50 in this example. The volume segments may be imaged in any desired order. In a preferred embodiment, abutting volume segments are imaged in succession, i.e., volume segment 120, followed by volume segment 122, followed by volume segment 124, etc. By imaging abutting segments in succession, adjacent image data is acquired from either the same cardiac cycle or consecutive cardiac cycles. Thus, discontinuities in the image data are minimized. In the imaging protocol of FIG. 5, a high resolution, three-dimensional image of the image volume is available after nine heartbeats.

Figure 6:
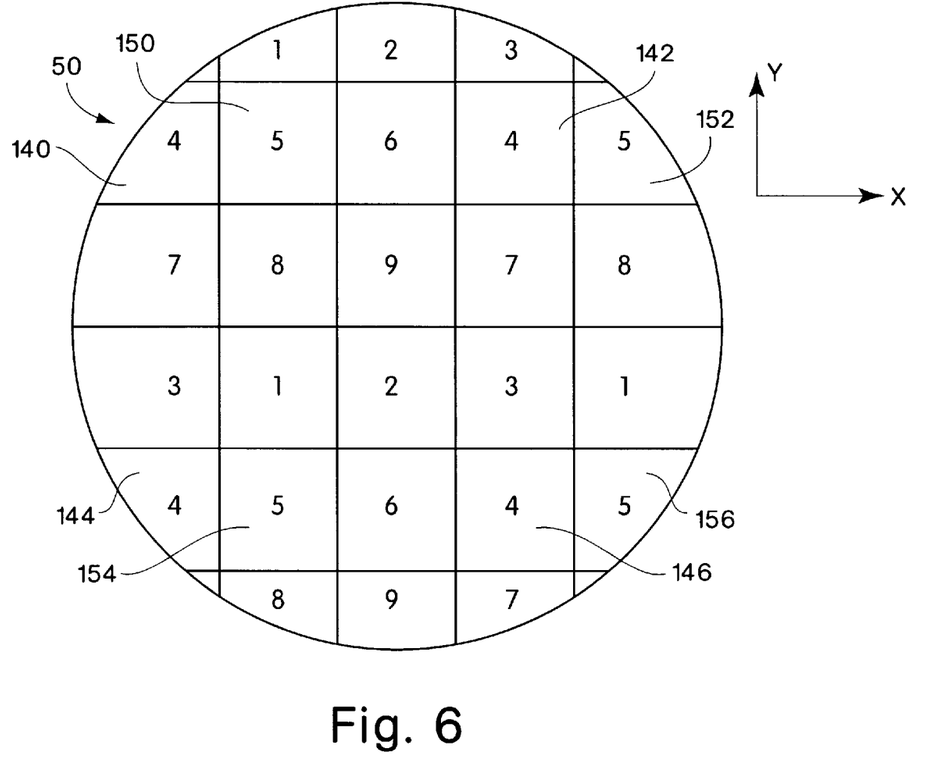
FIG. 6 is a cross-sectional view of a three-dimensional image volume that is divided into interleaved volume segments.

An example of an imaging protocol using interleaved volume segments is shown in FIG. 6. A cross section of conical image volume 50 is shown in FIG. 6. Image data is acquired for two or more spaced-apart volume segments during each cardiac cycle. Thus, for example during cardiac cycle CC4, image data for volume segments 140, 142, 146 is acquired. Similarly, during cardiac cycle CC5, image data for volume segments 150, 152, 154 and 156 is acquired. The volume segments for which image data is acquired during each cardiac cycle are distributed over the image volume. This imaging protocol permits a complete low resolution image of image volume 50 to be acquired in real time for each heartbeat. By combining image data from nine consecutive heartbeats, a high resolution image is produced. Thus, the user may view a low resolution image during data acquisition and may view a high resolution following completion of data acquisition. The user can, for example, select the high resolution image by pressing a button. A disadvantage of the interleaved volume segments is that motion between heartbeats causes a periodic discontinuity in the image data. It will be understood that a practical implementation may utilize image data acquisition for more than four spaced-apart volume segments during each cardiac cycle.

Different techniques may be used for acquiring image data within each of the volume segments. In one example, each volume segment includes two or more two-dimensional slices. However, any sequence for obtaining image data for each of the receive lines within the volume segment may be utilized. The selected sequence should be compatible with the technique used for providing delay data to the receive beamformer.

Figure 7:
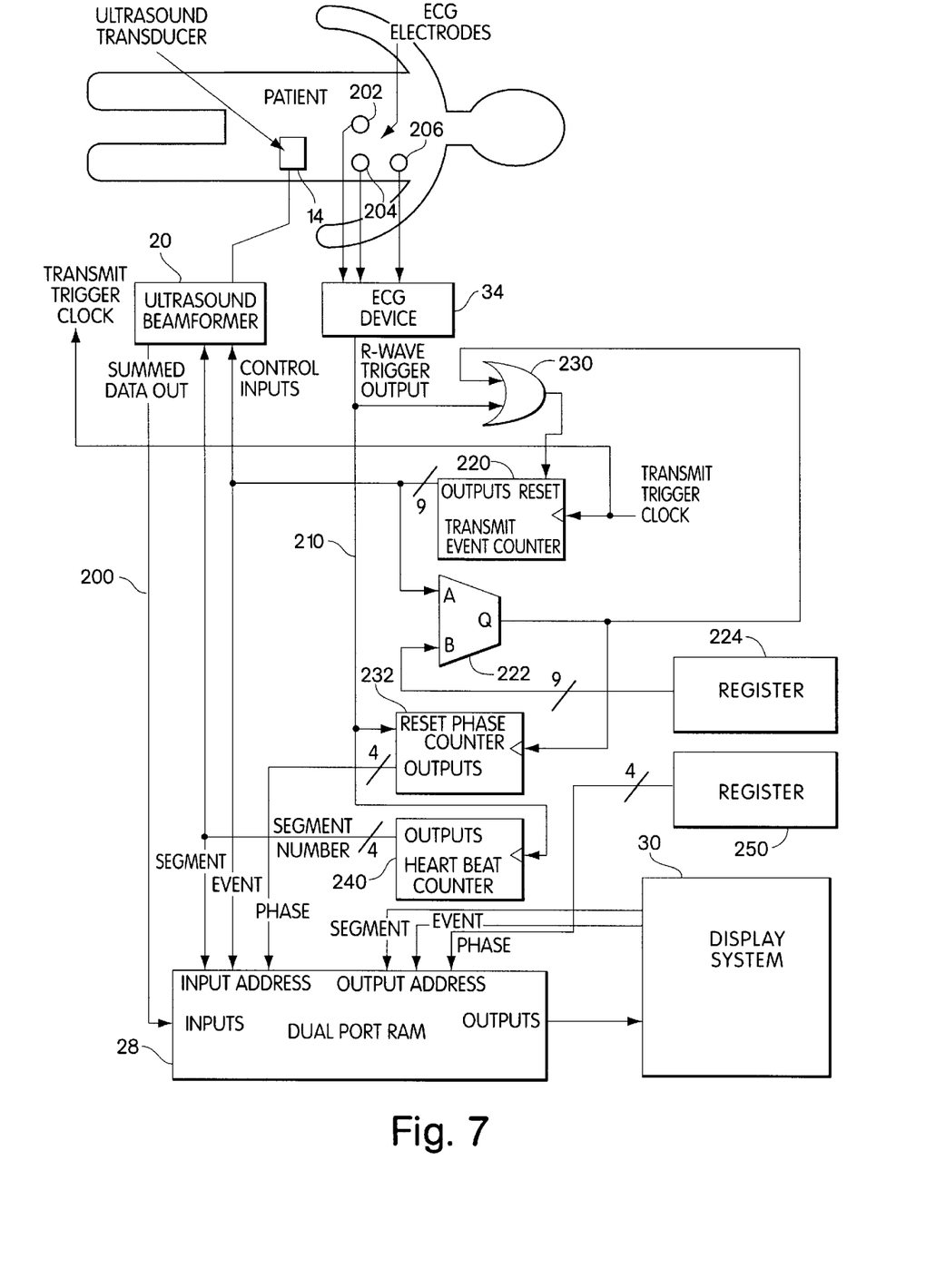
FIG. 7 is a schematic block diagram of an example of a system for cardiac ultrasound imaging in accordance with the invention.

A simplified block diagram of an example of a system for implementing segmented, three-dimensional cardiac imaging in accordance with the invention is shown in FIG. 7. Like elements in FIGS. 1 and 7 have the same reference numerals. Ultrasound energy is transmitted into the region of interest in the patient by transducer array 14. Transmitter 10, T/R switch 12 and receiver 16 are omitted from FIG. 7 for ease of understanding. The received ultrasound echoes are processed by beamformer 20 to provide image data on line 200. The image data is stored in image data buffer 28, which in the example of FIG. 7 is a dual port random access memory (RAM).

ECG electrodes 202, 204 and 206, attached to the patient, sense the patient's cardiac cycle and provide signals to ECG device 34. The ECG device 34 provide an R-wave trigger output on line 210. The R-wave trigger output corresponds to the ECG waveform shown in FIG.3.

A transmit trigger clock, which provides one pulse for each transmit event, is supplied to a transmit event counter 220 and to transmitter 10 (FIG. 1). The outputs of transmit event counter 220 are supplied to beamformer 20, to an event input address of image data buffer 28 and to a first input of a comparator 222. A register 224 stores the number of transmit events per cardiac phase. The outputs of register 224 are supplied to a second input of comparator 222. The output of comparator 222 is asserted when transmit event counter 220 reaches a count equal to the value stored in register 224. Thus, the output of comparator 222 is asserted when the required number of transmit events has been reached in each cardiac phase. The output of comparator is supplied to a first input of OR gate 230 and to the clock input of a cardiac phase counter 232. The outputs of phase counter 232, which indicate the cardiac phase for which image data is being acquired, are supplied to a phase input address of image data buffer 28.

The R-wave trigger output of ECG device 34 is supplied to a second input of OR gate 230, to the reset input of phase counter 232 and to the clock input of a heartbeat counter 240. The heartbeat counter 240 is incremented by the patient's heartbeats. The outputs of heartbeat counter 240 are supplied to a segment input address of image data buffer 28 and indicate the volume segment for which image data is being acquired. Thus, the input address of image data buffer 28 is made up of a segment input address which indicates volume segment, a phase input address which indicates cardiac phase and an event input address which indicates the transmit event within a specific volume segment and cardiac phase. The dual port RAM of image data buffer 28 may have locations for storage of image data corresponding to each transmit event of each volume segment of the image volume and corresponding to each phase of the patient's cardiac cycle.

The OR gate 230 supplies an output to the reset input of transmit event counter 220. Thus, transmit event counter is reset by the patient's heartbeat or when the comparator 222 indicates that the required number of transmit events has been completed for the current cardiac phase.

The output from image data buffer 28 is controlled by display system 30. Image data buffer 28 receives an output address, including a segment output address and an event output address from display system 30, and a cardiac phase output address from a register 250. Register 250 contains a value that indicates the cardiac phase to be displayed. The display system 30 combines the image data for the volume segments of the selected cardiac phase to produce a three-dimensional image of the image volume. By incrementing the value in register 250, three-dimensional images of different cardiac phases may be displayed in sequence. By incrementing to successive images at a suitable rate, images of heart movement may be displayed.

The control components of the imaging system of FIG. 7, including transmit event counter 220, comparator 222, OR gate 230, phase counter 232, heartbeat counter 240 and registers 224 and 250, may constitute part of system controller 32 (FIG. 1). It will be understood that the functions performed by these control components may be performed by a programmed microcomputer within the scope of the invention.

Figure 8:
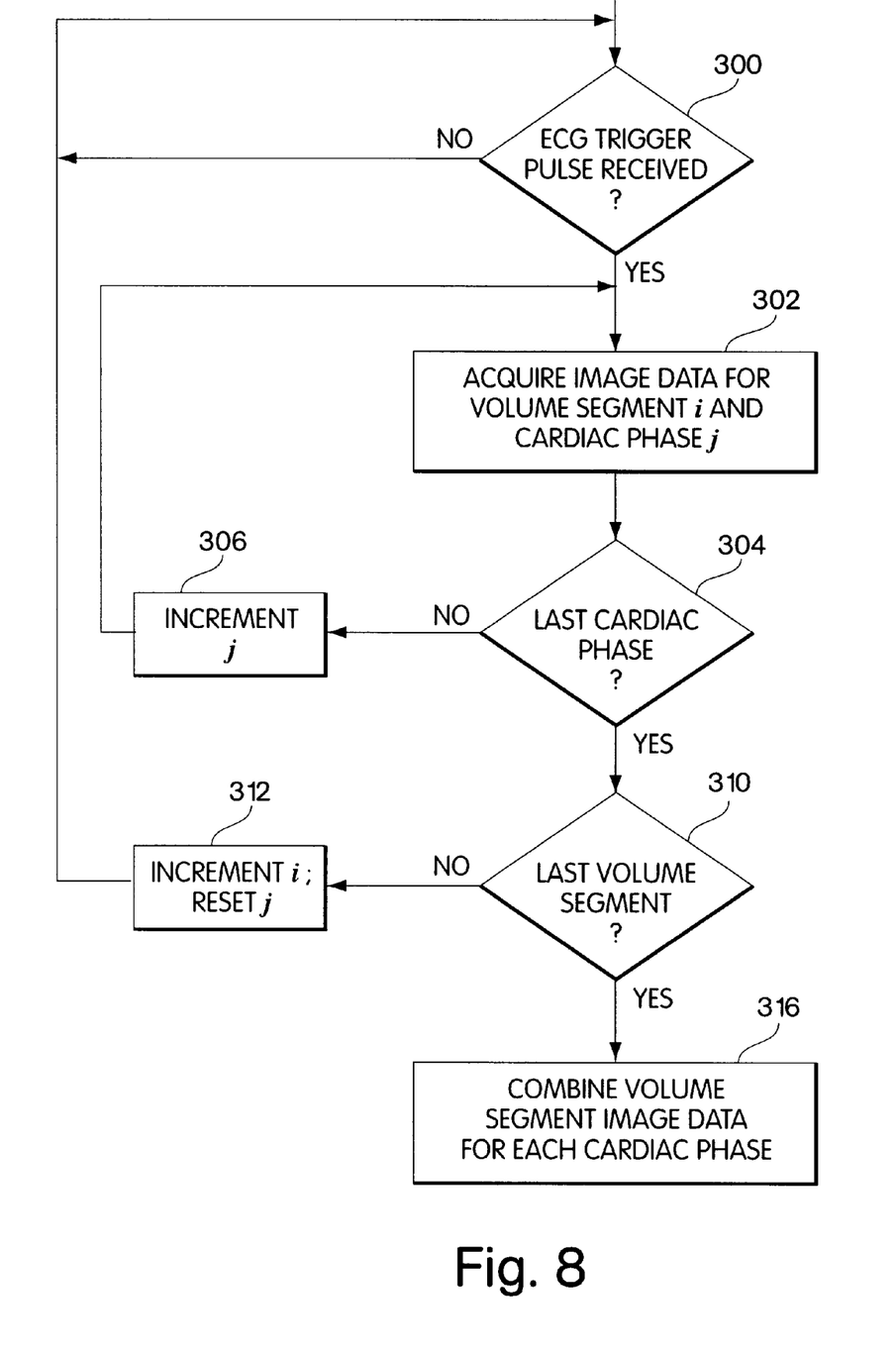
FIG. 8 is a flow diagram of an example of a method for cardiac ultrasound imaging in accordance with the invention.

A flowchart of a process for segmented three-dimensional cardiac imaging in accordance with the invention is shown in FIG. 8. When an ECG trigger pulse is received, as determined in step 300, image data is acquired for volume segment i and cardiac phase j in step 302. The data acquisition step 302 involves generation of the specified number of transmit events for the volume segment, processing the received signals in beamformer 20 to provide image data and storing the image data in image data buffer 28. In step 304, a determination is made as to whether the current cardiac phase is the last cardiac phase in the cardiac cycle. When the current cardiac phase is not the last cardiac phase, a cardiac phase index j is incremented in step 306, and the process returns to step 302 for acquisition of image data for the next cardiac phase of the same cardiac cycle. When the current cardiac phase is the last cardiac phase, a determination is made in step 310 as to whether image data has been acquired for the last volume segment of the image volume. When the current volume segment is not the last volume segment, a volume segment index i is incremented and the cardiac phase index j is reset in step 312. The process then returns to step 300 to wait for the next ECG trigger pulse.

The process of FIG. 8 performs image data acquisition for one or more volume segments during each phase of the patient's cardiac cycle. Complete three-dimensional images of each cardiac phase are acquired in a relatively small number of heartbeats. When image data for all volume segments of the image volume has been acquired, the volume segment image data is combined in step 316 to provide a composite image for each of the cardiac phases. The combining step involves combining image data for the volume segments of the image volume in the respective cardiac phases.

In another embodiment of the invention, the volume segments of the image volume may overlap. This approach requires somewhat more time for image data acquisition. However, the volume segments may be aligned by analyzing sets of image data in overlapping portions of the volume segments to determine offset error and shifting the image data in different volume segments so as to reduce the offset error.

The invention has been described in connection with acquisition of image data using a digital beamformer. It will be understood that the invention may be applied to analog implementations of ultrasound imaging systems.

While there have been shown and described what are at present considered the preferred embodiments of the present invention, it will be obvious to those skilled in the art that various changes and modifications may be made therein without departing from the scope of the invention as defined by the appended claims

What is claimed is:

1. A method for medical ultrasound imaging, comprising the steps
   a) acquiring ultrasound image data representative of three-dimensional volume segments of an image volume of interest in a patient in synchronism with corresponding cardiac cycles of the patient, each of said volume segments containing image data distributed in three dimensions, wherein image data representative of a volume segment is acquired during a single cardiac cycle of the patient; and b) combining the image data representative of said volume segments to provide image data representative of a three-dimensional ultrasound image of the image volume.

2. A method for medical ultrasound imaging as defined in claim 1 wherein the step of acquiring image data comprises synchronizing acquisition of said image data to a selected phase of the patient's cardiac cycle.

3. A method for medical ultrasound imaging as defined in claim 1 wherein the step of acquiring image data comprises acquiring image data for abutting volume segments in synchronism with successive cardiac cycles of the patient.

4. A method for medical ultrasound imaging as defined in claim 3 further comprising the step of displaying said three-dimensional ultrasound image following completion of the step of acquiring image data for said abutting volume segments.

5. A method for medical ultrasound imaging as defined in claim 1 wherein the step of acquiring image data comprises acquiring image data for interleaved volume segments in synchronism with successive cardiac cycles of the patient.

6. A method for medical ultrasound imaging as defined in claim 5 further comprising the step of displaying a low resolution image of the image volume during the step of acquiring image data for said interleaved volume segments.

7. A method for medical ultrasound imaging as defined in claim 5 further comprising the step of displaying said three-dimensional ultrasound image following completion of the step of acquiring image data for said interleaved volume segments.

8. A method for medical ultrasound imaging as defined in claim 1 further comprising the step of defining cardiac phases of the patient's cardiac cycle, wherein the step of acquiring image data comprises: (a1) acquiring image data for a three-dimensional volume segment during each of the cardiac phases of a cardiac cycle, and (a2) repeating step (a1) for different ones of said three-dimensional volume segments during different cardiac cycles.

9. A method for medical ultrasound imaging as defined in claim 8 wherein the step of combining comprises combining the volume segment image data for respective cardiac phases to provide three-dimensional ultrasound images representative of said cardiac phases.

10. A method for medical ultrasound imaging as defined in claim 1 wherein the volume segments of said image volume overlap, further comprising the step of aligning said volume segments by analyzing sets of image data in overlapping portions of said volume segments.

11. A method for medical ultrasound imaging as defined in claim 5 further comprising the steps of displaying a low resolution image of the image volume in response to user selection of a low resolution mode and displaying a high resolution image of the image volume in response to user selection of a high resolution mode.

12. A method for medical ultrasound imaging as defined in claim 1 wherein the step of acquiring image data comprises acquiring image data corresponding to different volume segments with different apertures of an ultrasound transducer.

13. A method for medical ultrasound imaging as defined in claim 5 wherein the image data for each of said interleaved volume segments represents a low resolution image of the image volume.

14. Apparatus for medical ultrasound imaging, comprising:
a transducer comprising an array of transducer elements;
a transmitter for transmitting ultrasound energy with said transducer into an image volume of interest in a patient's body as a plurality of transmit beams;
a receiver for receiving ultrasound echos with said transducer from the image volume in response to said ultrasound energy and for generating received signals representative of the received ultrasound echos;
a receive beamformer for processing said received signals to form at least one receive beam for each of said transmit beams and to generate image data representative of the ultrasound echos in said receive beam;
an ECG device coupled to the patient for generating an ECG signal representative of the patient's cardiac cycle;
a controller responsive to said ECG signal for controlling said transmitter and said receive beamformer to acquire image data representative of three-dimensional volume segments of the image volume in synchronism with corresponding cardiac cycles of the patient, each of said volume segments containing image data distributed in three dimensions, wherein image data representative of a volume segment is acquired during a single cardiac cycle of the patient; and
a combining circuit for combining the image data representative of said volume segments to provide image data representative of a three-dimensional ultrasound image of the image volume.

15. Apparatus as defined in claim 14 wherein said transducer comprises a two-dimensional array of transducer elements.

16. Apparatus as defined in claim 14 further comprising an image data buffer for storing said image data.

17. Apparatus as defined in claim 16 wherein said image data buffer comprises a dual port random access memory having an input port for receiving said image data from said receive beamformer and an output port for supplying said image data to said combining circuit.

18. Apparatus as defined in claim 14 wherein said controller further comprises means for synchronizing acquisition of said image data to a selected phase of the patient's cardiac cycle.

19. Apparatus as defined in claim 14 wherein said controller further comprises means for defining multiple cardiac phases of the patient's cardiac cycle, means for acquiring image data for a three-dimensional volume segment during each of the cardiac phases of a cardiac cycle, and means for repeating said data acquisition for different ones of said three-dimensional volume segments during different cardiac cycles.

20. Apparatus as defined in claim 19 wherein said combining circuit comprises means for combining the volume segment image data for respective cardiac phases to provide three-dimensional ultrasound images representative of each of said cardiac phases.

21. Apparatus as defined in claim 14 wherein said controller comprises means for acquiring image data for abutting volume segments in synchronism with successive cardiac cycles of the patient.

22. Apparatus as defined in claim 14 wherein said controller comprises means for acquiring image data for interleaved volume segments in synchronism with successive cardiac cycles of the patient.

23. Apparatus as defined in claim 22 further comprising means for displaying a low resolution image of the image volume during image data acquisition for said interleaved volume segments.

24. Apparatus for medical ultrasound imaging, comprising:
means for acquiring ultrasound image data representative of three-dimensional volume segments of an image volume of interest in a patient in synchronism with corresponding cardiac cycles of the patient, each of said volume segments containing image data distributed in three dimensions, wherein image data representative of a volume segment is acquired during a single cardiac cycle of the patient; and means for combining the image data representative of said volume segments to provide image data representative of a three-dimensional ultrasound image of the image volume.

25. A method for medical ultrasound imaging, comprising acquiring ultrasound image data representative of a three-dimensional volume segment of an image volume of interest in a patient during a single cardiac cycle of the patient, said volume segment containing image data distributed in three dimensions.

26. A method for medical ultrasound imaging, comprising the steps of:

(a) acquiring ultrasound image data representative of a three-dimensional volume segment of an image volume of interest in synchronism with a selected phase of the patient's cardiac cycle said volume segment containing image data distributed in three dimensions, wherein image data representative of the volume segment is acquired during a single cardiac cycle of the patient;

(b) repeating step (a) for a plurality of cardiac phases of the patient's cardiac cycle;

(c) repeating steps (a) and (b) for different three-dimensional volume segments of the image volume during different cardiac cycles of the patient; and (d) combining the volume segment image data for respective cardiac phases to provide three-dimensional ultrasound images that are respectively representative of said cardiac phases.

27. A method for medical ultrasound imaging as defined in claim 1 wherein said image data is acquired with an electronically scanned two-dimensional array of transducer elements.

28. A method for medical ultrasound imaging as defined in claim 1 wherein the three-dimensional ultrasound image of the image volume is acquired in a single breathhold of the patient.

29. A method for medical ultrasound imaging as defined in claim 9 wherein the image data representative of the three-dimensional ultrasound images is acquired during a single breathhold of the patient.

30. Apparatus as defined in claim 14 wherein said controller comprises means for acquiring the image data representative of the three-dimensional ultrasound image of the image volume in a single breathhold of the patient.

31. Apparatus as defined in claim 20 wherein said controller comprises means for acquiring the image data representative of the three-dimensional ultrasound images in a single breathhold of the patient.

32. Apparatus as defined in claim 24 wherein said means for acquiring comprises an electronically scanned two-dimensional array of transducer elements.

33. Apparatus as defined in claim 24 wherein said means for acquiring comprises means for acquiring image data representative of the three-dimensional ultrasound image volume in a single breathhold of the patient.

34. A method for medical ultrasound imaging as defined in claim 26 wherein the image data representative of the three-dimensional ultrasound images is acquired in a single breathhold of the patient.

* * * * *